United States Patent
Smith et al.

(10) Patent No.: US 11,939,611 B2
(45) Date of Patent: Mar. 26, 2024

(54) BIOCATALYTIC PROCESSES AND MATERIALS FOR ENHANCED CARBON UTILIZATION

(71) Applicant: INV Nylon Chemicals Americas, LLC, Wilmington, DE (US)

(72) Inventors: Gary Smith, Wilton (GB); Alex Van Eck Conradie, Eaglescliffe (GB); Gregory S. Kirby, Avondale, PA (US); Paul S. Pearlman, Thornton, PA (US)

(73) Assignee: INV NYLON CHEMICALS AMERICAS, LLC, Wilmington, DE (US)

( * ) Notice: Subject to any disclaimer, the term of this patent is extended or adjusted under 35 U.S.C. 154(b) by 226 days.

(21) Appl. No.: 15/436,315

(22) Filed: Feb. 17, 2017

(65) Prior Publication Data

US 2017/0240936 A1 Aug. 24, 2017

Related U.S. Application Data

(60) Provisional application No. 62/297,626, filed on Feb. 19, 2016.

(51) Int. Cl.
| | |
|---|---|
| C12P 13/00 | (2006.01) |
| C12M 1/00 | (2006.01) |
| C12M 1/34 | (2006.01) |
| C12N 1/20 | (2006.01) |
| C12P 5/00 | (2006.01) |
| C12P 5/02 | (2006.01) |
| C12P 7/06 | (2006.01) |
| C12P 7/24 | (2006.01) |
| C12P 7/625 | (2022.01) |
| C25B 1/04 | (2021.01) |
| F01D 15/10 | (2006.01) |
| F01K 7/16 | (2006.01) |
| F01K 11/02 | (2006.01) |

(52) U.S. Cl.
CPC .......... *C12P 13/001* (2013.01); *C12M 29/00* (2013.01); *C12M 41/00* (2013.01); *C12N 1/20* (2013.01); *C12P 5/00* (2013.01); *C12P 5/007* (2013.01); *C12P 5/02* (2013.01); *C12P 7/065* (2013.01); *C12P 7/24* (2013.01); *C12P 7/625* (2013.01); *C12P 13/00* (2013.01); *C25B 1/04* (2013.01); *F01D 15/10* (2013.01); *F01K 7/16* (2013.01); *F01K 11/02* (2013.01); *F05D 2220/31* (2013.01); *Y02E 50/10* (2013.01); *Y02E 50/30* (2013.01); *Y02E 60/36* (2013.01)

(58) Field of Classification Search
None
See application file for complete search history.

(56) References Cited

U.S. PATENT DOCUMENTS

| | | | |
|---|---|---|---|
| 4,957,861 A | 9/1990 | Lafferty et al. | |
| 2010/0069690 A1* | 3/2010 | Gudde | B01J 8/025 |
| | | | 585/240 |
| 2010/0317069 A1* | 12/2010 | Burk | C12N 1/38 |
| | | | 435/121 |
| 2012/0135480 A1* | 5/2012 | Nakas | C12P 7/625 |
| | | | 435/135 |

FOREIGN PATENT DOCUMENTS

| | | | |
|---|---|---|---|
| CN | 104903455 A | 9/2015 | |
| EP | 0520405 A2 | 12/1992 | |
| WO | WO-2011139804 A2 * | 11/2011 | ............... C12N 1/12 |
| WO | WO 2013/036635 A1 | 3/2013 | |

(Continued)

OTHER PUBLICATIONS

Chakraborty P et al. PHA Productivity and Yield of Ralstonia eutropha when intermittently or continuously fed a mixture of short chain fatty acids. 2012. Journal of Biomedicine and Biotechnology. p. 1-8 (Year: 2012).*

Cavalheiro JMBT et al. Poly(3-hydroxybutyrate) production by Cupriavidus necator using waste glycerol. 2009. Process Biochemistry. 509-515. (Year: 2009).*

Zhou C et al. Isopentenyl diphosphate and dimethylallyl diphosphate/isopentenyl diphosphate ratio measured with recombinant isopentenyl diphosphate isomerase and isoprene synthase. 2013. Analytical Biochemistry. 130-136. (Year: 2013).*

Ahn et al., (2011) "Butanol production from thin stillage using Clostridium pasteurianum," Bioresource Technology, 102(7): 4934-4937.

(Continued)

*Primary Examiner* — Paul J Holland

(57) ABSTRACT

The present disclosure describes biocatalytic processes for producing a product, comprising providing an aqueous stream (AS) comprising at least one fermentable substrate and a gaseous stream (GS) comprising at least one of $CO_2/H_2$, $H_2$, methane, and/or CO to a fermentation zone, wherein the GS and AS stream are optionally contacted and/or mixed; the fermentation zone comprising at least one organism capable of metabolizing an AS substrate and a GS substrate, wherein the fermentation operates at conditions to mixotrophically metabolize at least one gaseous substrate in the GS and at least one substrate in the AS, producing the product. The present disclosure also describes compositions comprising an AS, a GS, and an organism, wherein the organism or an equivalent or engineered equivalent thereof is a methanotroph or a hydrogen-metabolizing or CO-metabolizing chemolithotrophic organism, and wherein the organism is capable of mixotrophic metabolism of at least one gaseous substrate in the GS and at least one substrate in the AS. The present disclosure also describes a process wherein said fermentation operates at conditions to mixotrophically metabolize at least $H_2$ in the gaseous stream and glycerol and lactic acid in the aqueous stream. The present disclosure also describes a system for producing a fermentation or bio-derived product.

14 Claims, 9 Drawing Sheets

(56) References Cited

FOREIGN PATENT DOCUMENTS

| WO | WO-2015026870 A1 | * | 2/2015 | ............. C07C 29/76 |
| WO | WO 2016/138372 A1 | | 9/2016 | |

OTHER PUBLICATIONS

Fast et al., (2015) "Acetogenic mixotrophy: novel options for yield improvement in biofuels and biochemicals production," Current Opinion in Biotechnology, 33:60-72.

Ferreira et al., (2014) "Production of Ethanol and Biomass from Thin Stillage Using Food-Grade Zygomycetes and Ascomycetes Filamentous Fungi," Energies , 7, p. 3872.

Gonzalez et al., (2010) "Production of ethanol from thin stillage by metabolically engineered *Escherichia coli*," Biotechnology Letters , 32(3):405-411.

International Search Report dated Sep. 15, 2017, in International Application No. PCT/US2017/018375 (7 pages).

Karst et al., (1984) "Mixotrophic Capabilities of Alcaligenes eutrophus," Journal of General Microbiology, 130:1987-1994.

Kim et al., (2008) "Composition of corn dry-grind ethanol by-products: DDGS, wet cake, and thin stillage," Bioresource Technology, 99: 5165-5176.

Shi et al., (1997) "Metabolic Flux Analysis for Biosynthesis of Poly(b-Hydroxybutyric Acid) in Alcaligenes eutrophus from Various Carbon Sources," Journal of Fermentation and Bioengineering, 84(6): 579-587.

Linsey Garcia-Gonzalez et al., "Sustainable autotrophic production of polyhydroxybutyrate (PHB) from CO2 using a two-stage cultivation system," Catalysis Today, vol. 257, pp. 237-245 (2015).

Zhang, Shi-Min et al., "Screening of a PHB producing bacteria with glycerin as the carbon source and study on its fermentation conditions," Journal of Henan Agricultural University, vol. 47, No. 6, pp. 737-742 (2013) (Abstract).

First Office Action and Search Report received for CN application No. 201780013409.9, dated Jun. 2, 2021, 34 pages. (21 pages of English translation and 13 pages of Official copy).

* cited by examiner

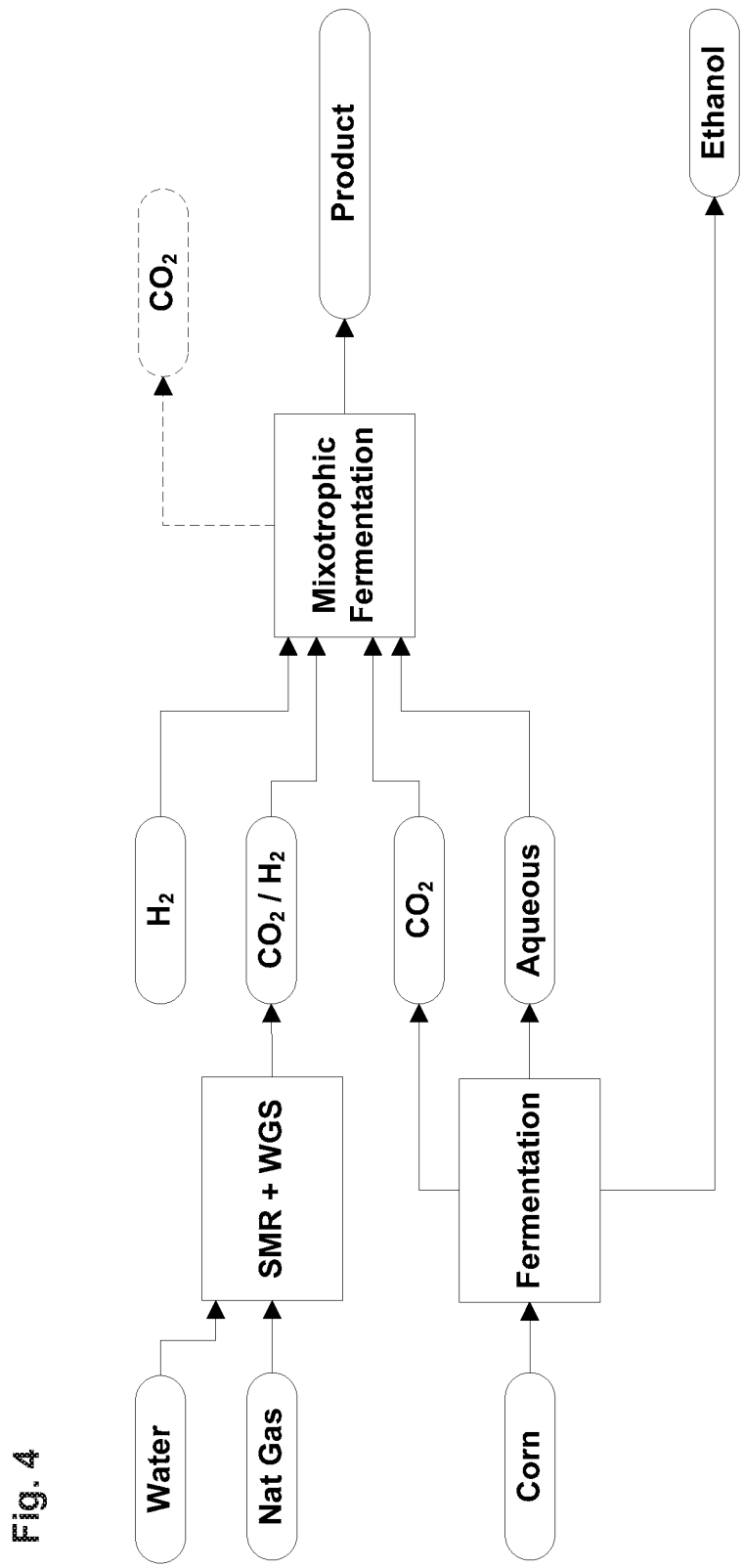

BIOCATALYTIC PROCESSES AND MATERIALS FOR ENHANCED CARBON UTILIZATION

This application claims priority to U.S. Provisional Patent Application No. 62/297,626, filed Feb. 19, 2016, the contents of which are incorporated herein by reference.

TECHNICAL FIELD

The present disclosure relates to biocatalytic processes, materials, and systems. In particular, the present disclosure relates to biocatalytic processes for producing a product which comprise providing an aqueous stream comprising more than one metabolizable substrate and/or an aqueous stream and a gaseous stream, or derivatives thereof, to a fermentation zone and simultaneously fermenting at least one substrate in the aqueous stream and at least one substrate in the gaseous stream and/or simultaneously fermenting more than one substrate in the aqueous stream.

BACKGROUND

The production of chemicals (e.g., ethanol) from biomass feedstocks is of commercial interest. For example, ethanol is generally produced using conventional fermentation processes that convert the starch in plant-based feedstocks into ethanol. However, conventional fermentation processes may only be able to convert limited concentrations of starch in these feedstocks or produce by-products of low value, and thus the spent fermentation stream may include fermentable starch and other materials as fermentation by-products. Described herein, are biocatalytic processes and systems to enhance carbon utilization in producing biomass-derived products, for example by use of fermentation by-products as feedstock for further fermentation.

In order to improve the economics of ethanol production, companies are looking at routes to upgrade lower valuable byproduct streams into higher value products. The spent fermentation stream (thin stillage), which is produced after the fermentation broth is treated to remove the undissolved solids and the ethanol, is typically concentrated to form a condensed corn distiller solubles (CDS) stream that is blended with the previously recovered solids to form a distiller dried grains and solubles (DDGS) product and is sold as animal feed. The DDGS product is a relatively low value product and there is interest in separating higher value components to increase the overall value of the system. The thin stillage stream contains potentially fermentable components that could be upgraded to more valuable products. A typical composition of thin stillage stream is shown in Table 1.

TABLE 1

A typical composition of thin stillage from cellulosic biomass compositional analysis (average of two batches).
Cellulosic biomass compositional analysis

| Dry matter (g/L) | 7.7 |
| Glucose (g/L) | 0.9 |
| Glucan (oligosaccharide, g/L) | 12.4 |
| Xylose (g/L) | 0.7 |
| Xylan (oligosaccharide, g/L) | 3.7 |
| Arabinose (g/L) | 0.4 |
| Arabinan (oligosaccharide, g/L) | 0.5 |
| Lactic acid (g/L) | 16.8 |
| Glycerol (g/L) | 14.4 |
| Acetic acid (g/L) | 0.3 |

TABLE 1-continued

A typical composition of thin stillage from cellulosic biomass compositional analysis (average of two batches).
Cellulosic biomass compositional analysis

| Butanediol (g/L) | 1.9 |
| Ethanol (g/L) | 0.6 |

(Kim, et. al Bioresource Technology 99 (2008) 5165-5176)

For a typical 50 million gallons per year (149 metric kilotonnes per year) ethanol plant, over 70 metric kilotonnes on a dry weight basis of thin stillage are produced a year, which includes almost 17 metric kilotonnes per year of glycerol and 19.5 metric kilotonnes per year of lactic acid. In addition to the thin stillage stream, a 50 million gallon per year ethanol plant also produces 150 metric kilotonnes per year of carbon dioxide off-gas, which is typically emitted to the atmosphere.

Glycerol is readily fermentable by a number of organisms, including *E. coli* (Gonzalez, et al., Biotechnology Letters, 2010, vol. 32, issue 3, pp 405-411) and *Clostridium pasteurianum* (Ahn, et al., Bioresource Technology, 2011, vol. 102, issue 7, pp 4934-4937]. These organisms may be used in systems that ferment glycerol in the thin stillage stream (or the concentrated distiller solubles produced from the thin stillage) to higher value products. Since fermentation processes co-produce carbon dioxide along with the desired products, the typical maximum yield of a product from glycerol is less than 50% (0.5 metric tonnes of product per metric tonne of available glycerol) with equal amounts of carbon dioxide also formed in the fermentation. For a 50 million gallon per year ethanol plant, this means that the maximum production capacity for a desired product is less than 8 metric kilotonnes per year.

Fast et al. (Current Opinion in Biotechnology, 2015, 33:60-72) utilize acetogenic anaerobic non-photosynthetic organisms that contain a Wood-Ljungdahl pathway, such as *Clostridium* sp., to increase the yield of products via mixotrophic fermentations by co-fermentation with carbohydrates and gaseous feed (e.g., $CO_2/H_2$, or CO). Yield increases based on carbohydrate feeds of 2-35% are demonstrated. *Clostridium* sp. are shown to produce a number of potential products including lactic acid.

In another example, Shi et al. (Journal of Fermentation and Bioengineering, Vol 84, No. 6, 579-587, 1997) demonstrate that *Cupriavidus necator* is capable of producing of poly($\beta$-hydroxybutyric acid) (PHB) and biomass from several acidic feedstocks, including acetic, lactic, and butyrate acids.

In another example (Karst et al., Journal of General Microbiology, 1984, 130, p. 1987-1994) an aerobic chemolithoautotrophic organism, such as *Cupriavidus necator*, is capable of mixotrophic growth with $CO_2/H_2$ and succinic acid to give production of poly($\beta$-hydroxybutyric acid) (PHB) and biomass.

Furthermore, filamentous fungi strains, such as *N. intermedia*, may be used for fermentation with wheat-based thin stillage in the industrial process of ethanol production (Ferreira et al., Energies, 2014, 7, p. 3872). *N. intermedia* cultivation may also be utilized to obtain food-grade biomass as a secondary product.

SUMMARY

In one or more embodiments, the present disclosure describes a biocatalytic process for producing a product, comprising: providing an aqueous stream (AS), and/or derivative thereof, comprising at least one fermentable substrate to a fermentation zone; providing a gaseous stream (GS) comprising at least one of $H_2$, $CO_2/H_2$, methane, and/or CO to the fermentation zone, wherein the GS and AS stream are optionally contacted and/or mixed; the fermentation zone comprising at least one organism capable of metabolizing an AS substrate and a GS substrate, wherein the fermentation operates at conditions to mixotrophically metabolize at least one gaseous substrate in the GS and at least one substrate in the AS; and forming at least one product via the fermentation.

In one or more embodiments, the present disclosure describes a composition comprising an AS, a GS, and an organism, wherein the organism or an equivalent or engineered equivalent thereof is a methanotroph or a hydrogen-metabolizing or CO-metabolizing chemolithotrophic organism, and wherein the organism is capable of mixotrophic metabolism of at least one gaseous substrate in the GS and at least one substrate in the AS.

In one or more embodiments, the present disclosure describes a system for producing a fermentation or bio-derived product, comprising a member to provide an AS or derivative thereof to a fermentation zone; a member to provide a GS or derivative thereof to a fermentation zone; a fermentation zone, the fermentation zone comprising at least one organism capable of mixotrophic metabolism of an AS substrate and a GS substrate, wherein the fermentation operates at conditions to simultaneously ferment at least one gaseous substrate in the GS and at least one substrate present in the AS; one of more fermentation zone control members, to control the conditions for fermenting; and a zone for treating the product.

In one or more embodiments, the present disclosure describes a biocatalytic process for producing a product, comprising: providing an aqueous stream (AS) and/or derivative thereof having at least one fermentable substrate to a fermentation zone; providing a gaseous stream (GS) comprising at least one of $H_2$, $CO_2/H_2$, methane, and CO to the fermentation zone, the fermentation zone comprising at least one organism capable of metabolizing at least one substance in the AS substrate; wherein the AS comprises (1) at least one polyol such glycerol, carbohydrates, or oligomers of carbohydrate, and (2) a carboxylic acid such as acetic acid, lactic acid, succinic acid or butyric acid; and wherein the organism is capable of metabolizing at least one substance in the GS.

In one or more embodiments, the present disclosure describes a biocatalytic process for producing a product, comprising: providing an aqueous stream (AS) and/or derivative thereof having at least glycerol and lactic acid to a fermentation zone; providing a gaseous stream (GS) comprising $H_2$ or optional $CO_2/H_2$, to the fermentation zone, the fermentation zone comprising at least one organism capable of metabolizing glycerol and lactic acid and wherein the organism is capable of metabolizing at least one substance in the GS.

In one or more embodiments, the present disclosure describes a biocatalytic process for producing a product, comprising: providing an aqueous stream (AS) and/or derivative thereof having at least glycerol and lactic acid to a fermentation zone; providing a gaseous stream (GS) comprising $H_2$ or optional $CO_2/H_2$, to the fermentation zone, the fermentation zone comprising at least one *Cupriavidus necator* organism capable of metabolizing glycerol and lactic acid and wherein the organism is capable of metabolizing at least one substance in the GS.

In one or more embodiments, the present disclosure describes a biocatalytic process for producing a product, comprising: providing an aqueous stream (AS) from the spent fermentation broth and/or derivative thereof having at least one fermentable substrate to a fermentation zone; providing a gaseous stream (GS) comprising $H_2$ or optional $CO_2/H_2$, to the fermentation zone, the fermentation zone comprising at least one organism capable of metabolizing glycerol and lactic acid and wherein the organism is capable of metabolizing at least one substance in the GS.

In one or more embodiments, providing a gaseous stream (GS) is optional. In some embodiments the present disclosure describes a biocatalytic process for producing a product, comprising providing an aqueous stream (AS), and/or derivative thereof, comprising (1) at least one polyol such glycerol, carbohydrates, or oligomers of carbohydrate, and (2) a carboxylic acid such as acetic acid, lactic acid, succinic acid or butyric acid; the fermentation zone comprising at least one organism capable of simultaneously metabolizing at least one of the polyols and at least one of the carboxylic acids, wherein the fermentation operates at conditions to metabolize at least one of the polyols and at least one of the carboxylic acids in the AS; and forming at least one product via the fermentation.

In one or more embodiments, the present disclosure describes a composition comprising an AS and an organism, wherein the organism or an equivalent or engineered equivalent thereof is a capable of simultaneous metabolism of (1) at least one polyol such glycerol, carbohydrates, or oligomers of carbohydrate, and (2) a carboxylic acid such as acetic acid, lactic acid, succinic acid or butyric acid in the AS.

In one or more embodiments, the present disclosure describes a system for producing a fermentation or bio-derived product, comprising a member to provide an AS containing (1) at least one polyol such glycerol, carbohydrates, or oligomers of carbohydrate, and (2) a carboxylic acid such as acetic acid, lactic acid, succinic acid or butyric acid or derivative thereof to a fermentation zone; a fermentation zone, the fermentation zone comprising at least one organism capable of mixotrophic metabolism of (1) at least one polyol such glycerol, carbohydrates, or oligomers of carbohydrate, and (2) a carboxylic acid such as acetic acid, lactic acid, succinic acid or butyric acid an AS substrate, wherein the fermentation operates at conditions to simultaneously ferment (1) at least one polyol such glycerol, carbohydrates, or oligomers of carbohydrate, and (2) a carboxylic acid such as acetic acid, lactic acid, succinic acid or butyric acid present in the AS; one of more fermentation zone control members, to control the conditions for fermenting; and a zone for treating the product.

In one or more embodiments, the present disclosure describes a biocatalytic process for producing a product, comprising: providing an aqueous stream (AS) and/or derivative thereof having (1) at least one polyol such glycerol, carbohydrates, or oligomers of carbohydrate, and (2) a carboxylic acid such as acetic acid, lactic acid, succinic acid or butyric acid to a fermentation zone; the fermentation zone comprising at least one organism capable of metabolizing (1) at least one polyol such glycerol, carbohydrates, or oligomers of carbohydrate, and (2) a carboxylic acid such as acetic acid, lactic acid, succinic acid or butyric acid in the AS substrate.

In one or more embodiments, the present disclosure describes a biocatalytic process for producing a product, comprising: providing an aqueous stream (AS) and/or derivative thereof having (1) glycerol, and (2) a, lactic acid, to a fermentation zone; the fermentation zone comprising at least one organism capable of metabolizing glycerol and lactic acid.

In one or more embodiments, the present disclosure describes a biocatalytic process for producing a product, comprising: providing an aqueous stream (AS) and/or derivative thereof having (1) glycerol, and (2) lactic acid, to a fermentation zone; the fermentation zone comprising at least one *Cupriavidus necator* organism capable of metabolizing glycerol and lactic acid.

DESCRIPTION OF DRAWINGS

The descriptions below are provided by way of explanation. The disclosures of the figures are not limited to the descriptions below.

FIG. 4 is a schematic of (1) providing corn biomass as feedstock to a first fermentation zone, producing a $CO_2$ stream, an aqueous stream, and an ethanol stream, (2) providing water and a natural gas stream to a steam methane reformation (SMR) and water gas shift (WGS) zone, producing a stream comprising $CO_2$ and/or $H_2$, (3) providing the $CO_2$ stream, the aqueous stream, the $CO_2/H_2$ stream, and an $H_2$ stream to a second fermentation zone, producing a product and, optionally, $CO_2$ by mixotrophic fermentation.

DETAILED DESCRIPTION

Figure 1:
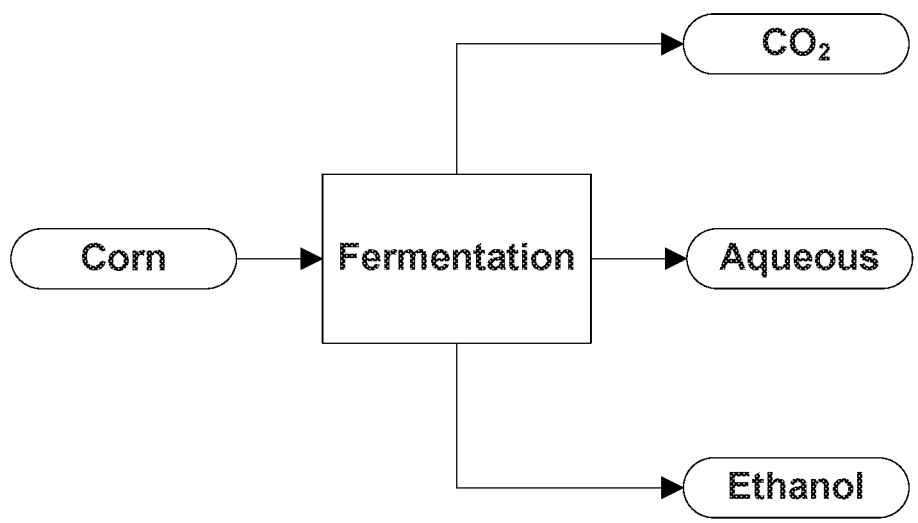
FIG. 1 is a schematic of providing corn biomass as feedstock to a fermentation zone and producing a $CO_2$ stream, an aqueous stream, and an ethanol stream.
Figure 2:
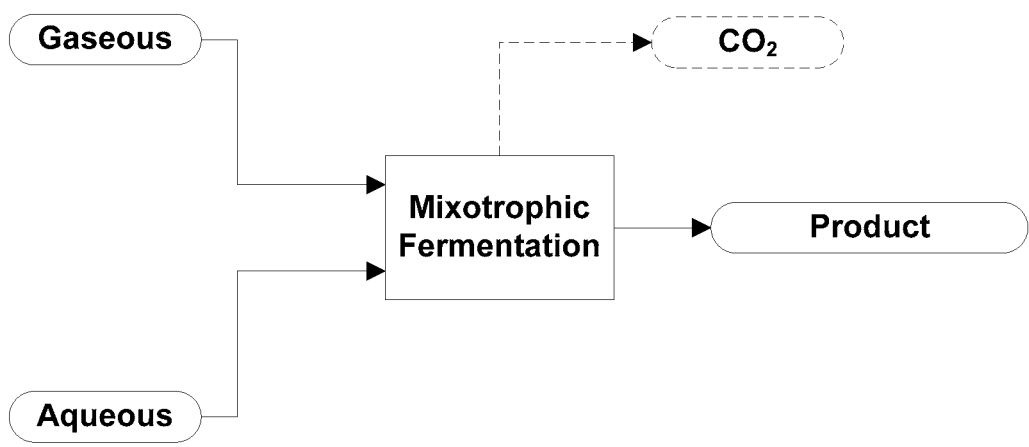
FIG. 2 is a schematic of providing a gaseous stream and an aqueous stream to a fermentation zone and producing a product and, optionally, $CO_2$ by mixotrophic fermentation.
Figure 3A:
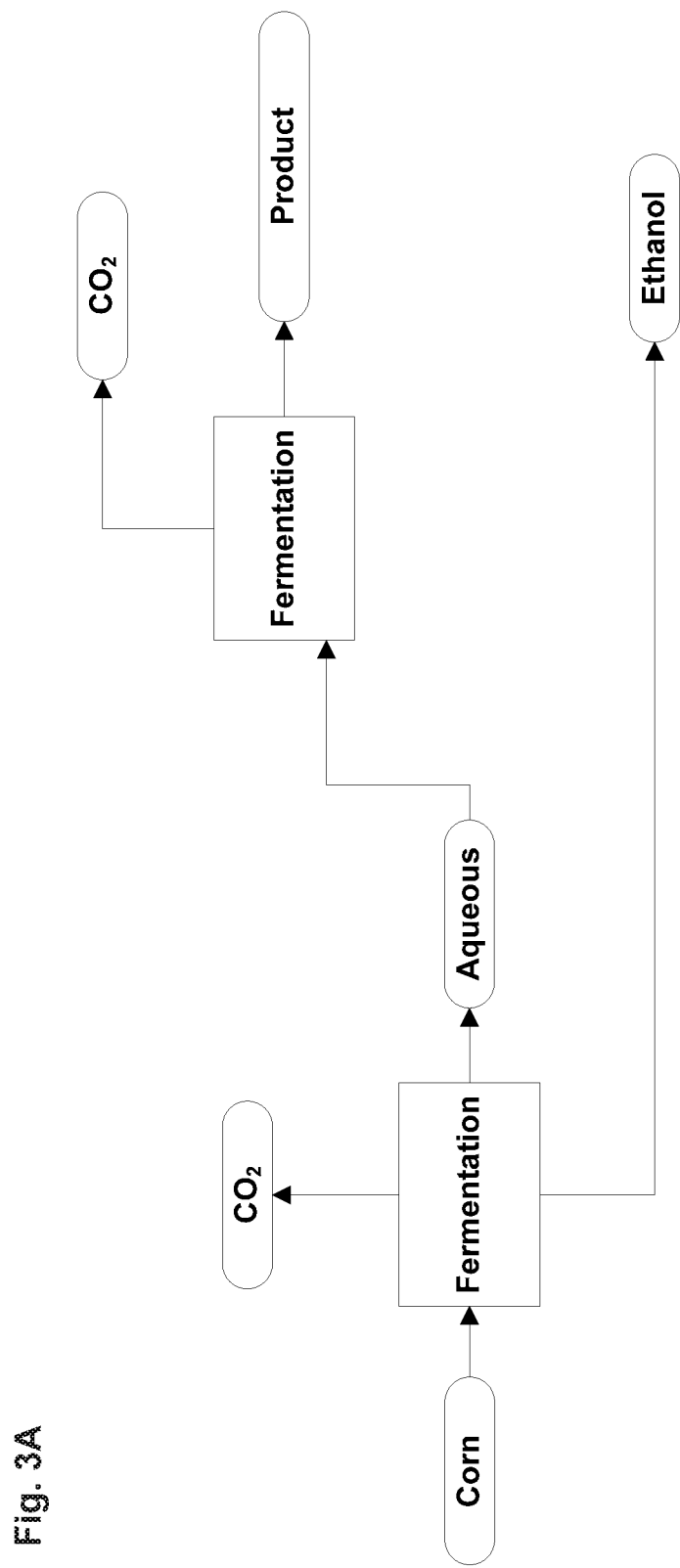
FIG. 3A is a schematic of providing corn biomass as feedstock to a first fermentation zone, producing a $CO_2$ stream, an aqueous stream, and an ethanol stream, wherein the aqueous stream, is subsequently provided to a second fermentation zone, producing a product and $CO_2$ by fermentation.
Figure 3B:
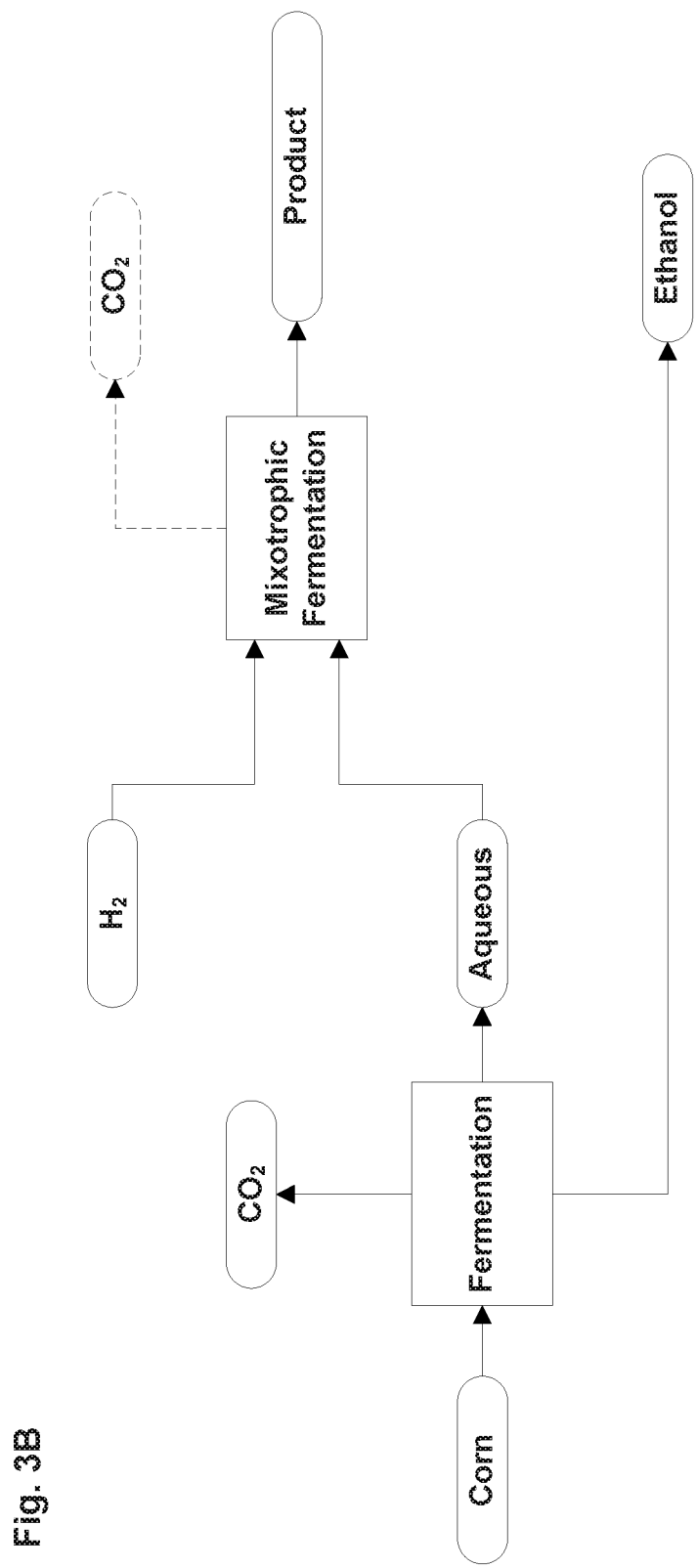
FIG. 3B is a schematic of providing corn biomass as feedstock to a first fermentation zone, producing a $CO_2$ stream, an aqueous stream, and an ethanol stream, wherein the aqueous stream, and an $H_2$ stream are subsequently provided to a second fermentation zone, producing a product and, optionally, $CO_2$ by mixotrophic fermentation.
Figure 3C:
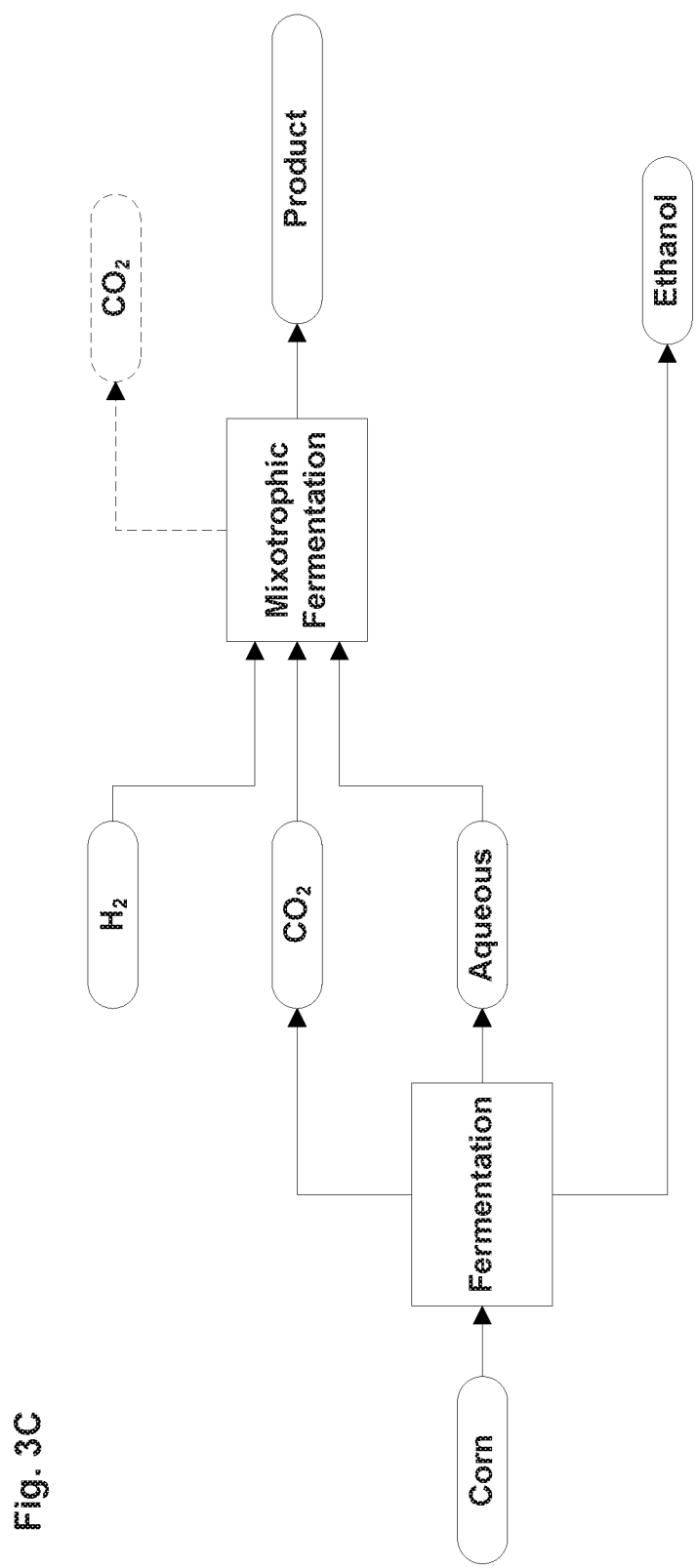
FIG. 3C is a schematic of providing corn biomass as feedstock to a first fermentation zone, producing a $CO_2$ stream, an aqueous stream, and an ethanol stream, wherein the $CO_2$ stream, the aqueous stream, and an $H_2$ stream are subsequently provided to a second fermentation zone, producing a product and, optionally, $CO_2$ by mixotrophic fermentation.
Figure 5:
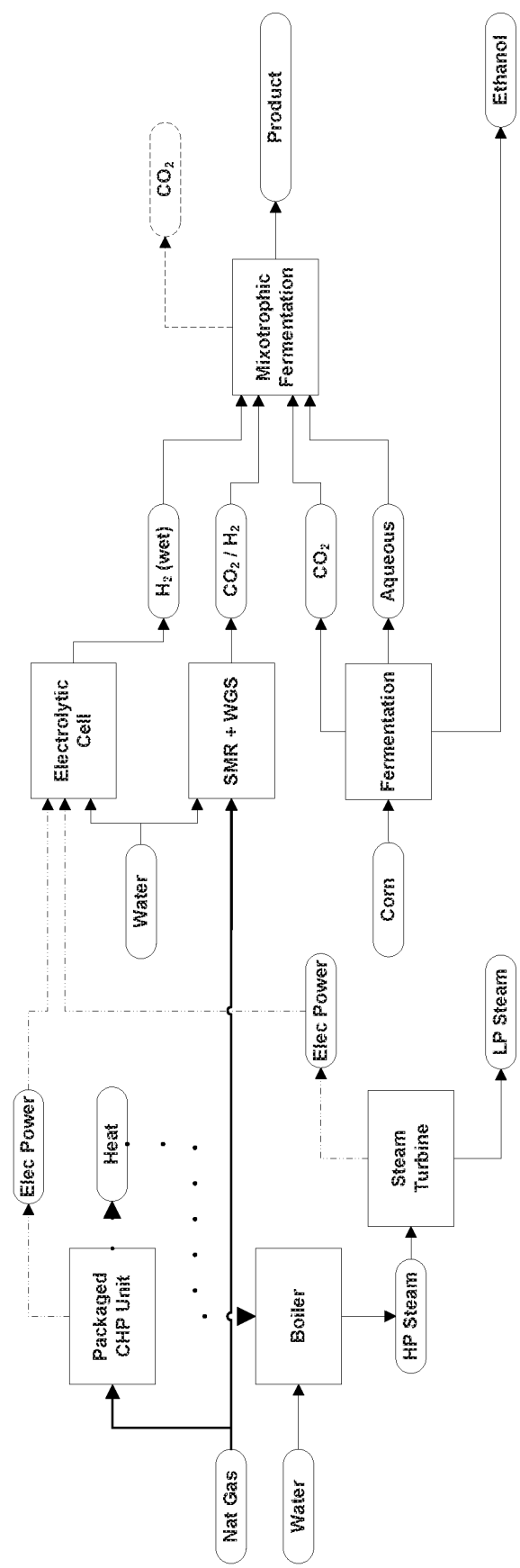
FIG. 5 is a schematic of a process wherein (1) combustion of natural gas in a combined heat and power (CHP) unit generates power driving an electrolytic cell and generates heat driving a boiler producing high pressure steam which drives a steam turbine producing electric power driving an electrolytic cell, the electrolytic cell producing $H_2$ by water electrolysis for use in a mixotrophic fermentation process similar to that shown in FIG. 4 and described above, (2) $CO_2$ and/or $H_2$ for use in a mixotrophic fermentation process similar to that shown in FIG. 4 and described above are derived from natural gas by a steam methane reformation (SMR) process, optionally comprising a water gas shift (WGS) process; (3) a product and, optionally, $CO_2$ are produced by mixotrophic fermentation in a process similar to that shown in FIG. 4 and described above.
Figure 6:
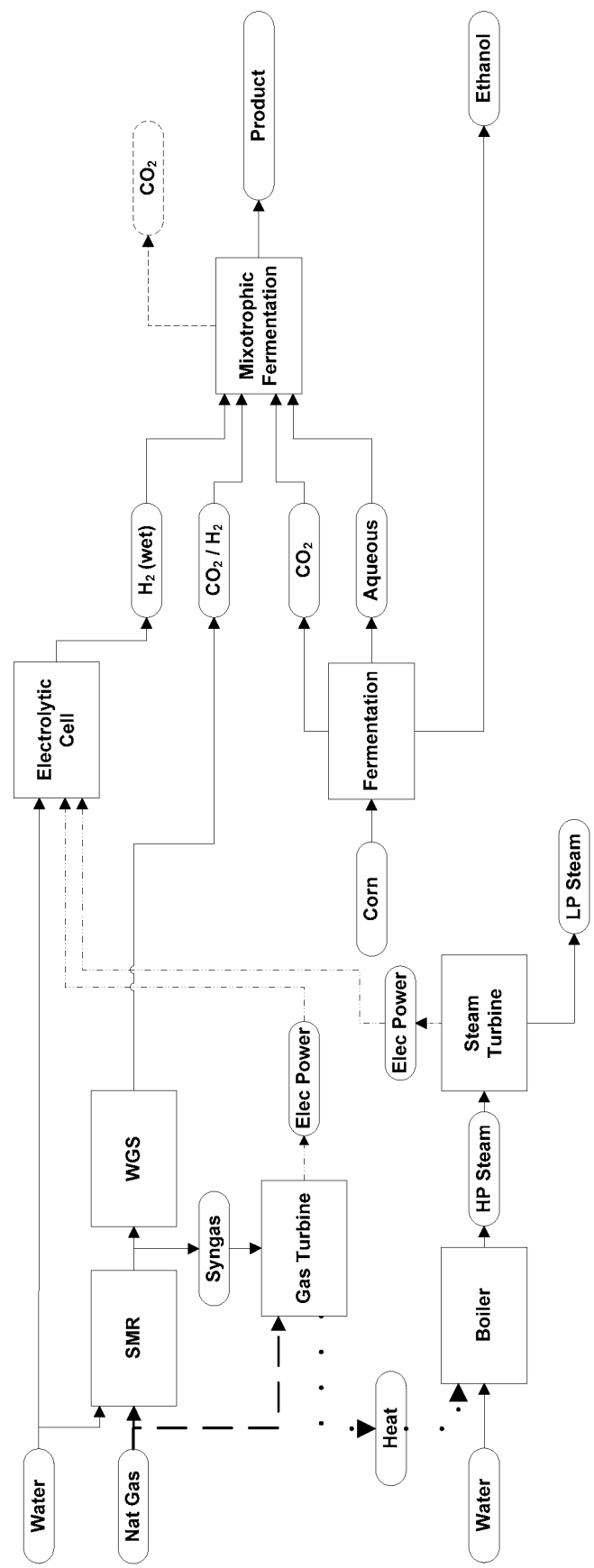
FIG. 6 is a schematic of a process wherein (1) $CO_2$ and/or $H_2$ for use in a mixotrophic fermentation process similar to that shown in FIG. 4 and described above are derived from natural gas by a steam methane reformation (SMR) process, optionally comprising a water gas shift (WGS) process; (2) natural gas or syngas recovered from the WGS process may be used to power a gas turbine producing electric power, driving an electrolytic cell, the electrolytic cell producing $H_2$ by water electrolysis; (3) heat produced by the gas turbine may be used to drive a boiler producing high pressure steam driving a steam turbine producing electric power driving an electrolytic cell, the electrolytic cell producing $H_2$ by water electrolysis; (4) $H_2$ for use in a mixotrophic fermentation process similar to that shown in FIG. 4 and described above is produced by water electrolysis; (5) a product and, optionally, $CO_2$ are produced in a mixotrophic fermentation process similar to that shown in FIG. 4 and described above.
Figure 7:
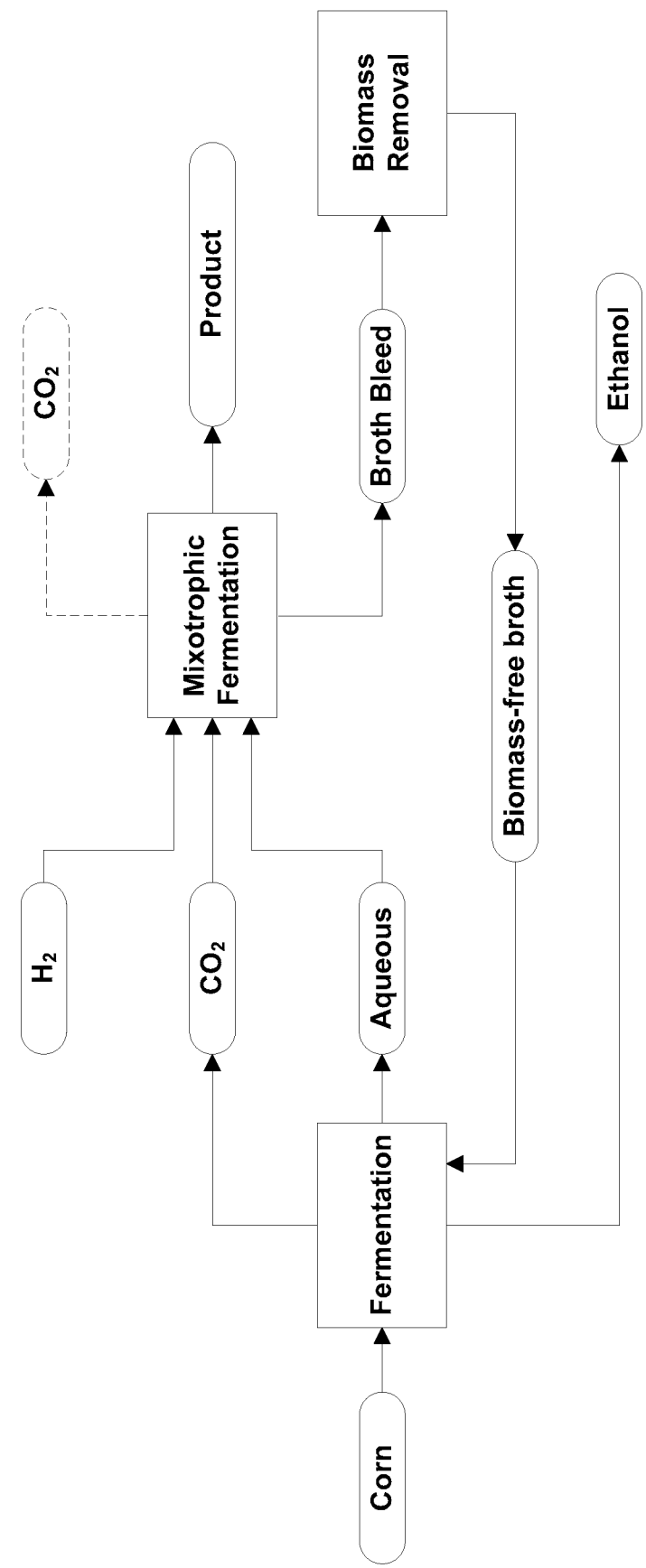
FIG. 7 is a schematic of a process (1) providing corn biomass as feedstock to a first fermentation zone, producing a $CO_2$ stream, an aqueous stream, and an ethanol stream; (2) wherein at least some of the $CO_2$ stream, the aqueous stream, and an $H_2$ stream are subsequently provided to a second fermentation zone, producing a product and, optionally, $CO_2$ by mixotrophic fermentation; (3) wherein broth bleed from the second fermentation zone is treated by biomass removal and the resulting biomass-free broth is provided to the first fermentation zone.

It is to be understood that both the foregoing general description and the following detailed description are exemplary and explanatory only and are not restrictive of the invention, as claimed.

The disclosures herein include biocatalytic processes, biocatalysts, fermentation or bio-derived products, compositions comprising products produced by biocatalytic processes, compositions comprising fermentation or bio-derived products, compositions comprising biocatalysts for biocatalytic processes, systems for producing fermentation or bio-derived products, and organisms for use in biocatalytic processes.

In some embodiments, the biocatalytic processes disclosed herein may allow improved carbon utilization by using as feedstock for further fermentation the co-products of a first biomass fermentation process, for example the co-products of a corn fermentation process, such as the co-products of a process producing bio-ethanol from corn feedstock. In some embodiments, the biocatalytic processes disclosed herein consume co-products of a first biomass fermentation process and upgrade those co-products to products of greater value. In some embodiments, the co-products of a first biomass fermentation process that are of interest as feedstocks for biocatalytic processes disclosed herein include, but are not limited to, $CO_2$ off-gas and fermentable constituents of stillage.

The present disclosure relates in part to biocatalytic processes for producing a product which comprise providing an aqueous stream (AS) and a gaseous stream (GS), or derivatives thereof, to a fermentation zone and mixotrophically metabolizing at least one substrate in the aqueous stream and at least one substrate in the gaseous stream. In some embodiments, the AS and GS are mixed prior to being provided to the fermentation zone. In some embodiments, the AS and GS are mixed in the fermentation zone, initially, regularly, or continually.

The present disclosure relates in part to biocatalytic processes for producing a product which comprise providing an aqueous stream (AS) comprising (1) at least one polyol such glycerol, carbohydrates, or oligomers of carbohydrate, and (2) a carboxylic acid such as acetic acid, lactic acid, succinic acid or butyric acid, to a fermentation zone and simultaneously metabolizing (1) at least one polyol such glycerol, carbohydrates, or oligomers of carbohydrate, and (2) a carboxylic acid such as acetic acid, lactic acid, succinic acid or butyric acid.

In some embodiments, the aqueous stream comprises at least one of a spent fermentation stream, stillage from a bio-ethanol production process, thin stillage stream from a bio-ethanol production process, concentrated corn distiller soluble (CDS), whole stillage stream from a bio-ethanol production process, glycerol, carbohydrates, oligomers of carbohydrate, protein, carboxylic acid, acetic acid, lactic acid, or an aqueous stream derived thereof.

As used herein, "spent fermentation stream" means the remainder of a fermentation process after removal of the product, including but not limited to fermentation by-products and unreacted feedstock.

As used herein, "whole stillage" means the liquid and solid remainders of a fermentation process after removal of the product.

As used herein, "thin stillage" means the liquid remainder of a fermentation process after removal of the product.

As used herein, "condensed corn distiller soluble" (CDS) means concentrated thin stillage after removal of at least a portion of the water. Herein, thin stillage shall include CDS.

As used herein, "bio-ethanol" means ethanol derived from biomass feedstock.

In at least one embodiment, the AS is obtained from a milled ethanol production process, for example a corn or wheat milled ethanol production process.

In some embodiments, the AS comprises compounds selected from organic acids, fatty acids, polyols, glycerol, carbohydrates, and oligomers of carbohydrate, peptides, polypeptides, betaines, carbohydrates, vitamins, and enzymes. For example, the AS can comprise organic acids such as succinic acid, lactic acid, acetic acid, citric acid, fumaric acid, folic acid, and phytic acid. For example, the AS can comprise fatty acids such as saturated, monounsaturated, and polyunsaturated fatty acids. For example, the AS can comprise fatty acids such as lauric acid, myristic acid, palmitic acid, stearic acid, oleic acid, palmitoleic acid, vaccenic acid, myristoleic acid, erucic acid, linoleic acid, linolenic acid, arachidonic acid, eicopentanoic acid, docosahexanoic acid, as well as fatty acids having a longer or shorter carbon chain, or greater or fewer carbon bonds than those listed here, and/or double bonds arranged in a cis or trans configuration. For example, the AS can comprise carbohydrates such as monosaccharides, disaccharides, oligosaccharides, polysaccharides, each of which can include sugar alcohols as their entire structure or as a portion of their structure.

In at least one embodiment, the AS comprises (1) at least one glycerol, carbohydrates, or oligomers of carbohydrate, and (2) a carboxylic acid. For example, the carboxylic acid may be selected from the group consisting of a fatty acid, lactic acid, and acetic acid.

In at least one embodiment, the AS comprises (1) at least one glycerol, and (2) lactic acid.

In at least one embodiment the AS is derived from a bioethanol process.

In some embodiments of biocatalytic processes as herein described, a fermentation broth bleed stream means a portion of the fermentation broth that is diverted from the fermentation zone, wherein components of the bleed stream may be optionally added back to the fermentation broth.

In some embodiments of biocatalytic processes as herein described, a fermentation broth bleed stream is removed from the fermentation zone, treated to remove biomass, and the resulting biomass-free broth is provided to the fermentation zone, recycling the broth bleed stream. In at least one embodiment, recycling of broth bleed stream allows improved utilization of the feedstock. Recycling of broth bleed stream as presently described can allow improved carbon utilization in biomass fermentation systems by recovery of fermentable constituents of thin stillage without need for an evaporation step.

In some embodiments, the gaseous stream comprises $H_2$. In some embodiments, the gaseous stream comprises syngas. In some embodiments, the gaseous stream comprises $CO_2/H_2$, $H_2$ and/or CO. In some embodiments, the gaseous stream comprises $CO_2$ and/or $H_2$, either or both of which may be obtained from a steam methane reformation (SMR) process, which may optionally further comprise a water gas shift (WGS) process.

In some embodiments, the gaseous stream comprises $CO_2$ and/or $H_2$ and in the fermentation zone the GS has a $CO_2:H_2$ molar ratio ranging from 0 to 0.35 mol $CO_2$/mol $H_2$. In another embodiment the GS has a $CO_2:H_2$ molar ratio ranging from 0.15 to 0.25 mol $CO_2$/mol $H_2$. In one embodiment pure $H_2$ may be fed and the only source of $CO_2$ may be from the AS, e.g. from metabolism of thin stillage. In another embodiment the GS may be low in $H_2$.

In some embodiments, the gaseous stream comprises natural gas. In some embodiments, the GS is derived from natural gas, for example natural gas which may be combusted in at least one combined heat and power (CHP) unit to generate power. In at least one embodiment, the power generated in the CHP unit is used for $H_2$ production via water electrolysis. In at least one embodiment, the $H_2$ produced by water electrolysis is used in fermentation processes described herein. In at least one embodiment, the CHP unit generates steam, which may be used to drive a turbo generator for generating electric power. The electric power generated may be exported, exported for use in biocatalytic processes described herein, exported for use in bio-ethanol production, and/or provide for $H_2$ and $O_2$ production, thereby producing $H_2$ for use in fermentation processes described herein. In at least one embodiment the generated power provides for $H_2$ production via water electrolysis, thereby producing $H_2$ and $O_2$. In at least one embodiment $H_2$ thus produced is used in biocatalytic processes as described herein. In at least one embodiment $O_2$ thus produced is used in biocatalytic processes as described herein.

In some embodiments, at least a portion of the gaseous stream is provided to a gas combustion turbo-generator to generate power. In one embodiment, the power thus produced provides for $H_2$ production via water electrolysis, thereby producing $H_2$ and $O_2$. In at least one embodiment $H_2$ thus produced is used in biocatalytic processes as described herein. In at least one embodiment $O_2$ thus produced is used in biocatalytic processes as described herein.

In some embodiments, at least a portion of the gaseous stream drives a non-combusting turbo generator to generate power. In one embodiment the power thus produced provides for $H_2$ production via water electrolysis, thereby producing $H_2$ and $O_2$. In at least one embodiment $H_2$ thus produced is used in biocatalytic processes as described herein. In at least one embodiment $O_2$ thus produced is used in biocatalytic processes as described herein.

In some embodiments, at least a portion of the gaseous stream is provided to a steam methane reformation (SMR)

process for producing syngas. In at least one embodiment, at least a portion of the syngas thus produced is provided to a gas turbo-generator to generate power. In some embodiments, at least a portion of the gaseous stream is provided to a steam methane reformation (SMR) process for producing $CO_2$, $H_2$ and/or CO. In at least one embodiment, at least a portion of the $CO_2$, $H_2$ and/or CO thus produced is provided to a gas turbogenerator to generate power. In one embodiment the power thus produced provides for $H_2$ production via water electrolysis, thereby producing $H_2$ and $O_2$. In at least one embodiment $H_2$ thus produced is used in biocatalytic processes as described herein. In at least one embodiment $O_2$ thus produced is used in biocatalytic processes as described herein.

In the biocatalytic processes described herein, the fermentation zone comprises at least one organism capable of metabolizing an AS substrate and a GS substrate and the fermentation operates at conditions to mixotrophically metabolize at least one gaseous substrate in the GS and at least one gaseous substrate in the AS. As used herein, "mixotrophically metabolize" means metabolize different sources of energy and carbon. Thus, the at least one organism is an organism that can utilize substrates from diverse sources, for example an organism capable of metabolizing at least one substrate from the AS and at least one substrate from the GS at the fermentation zone conditions.

In some embodiments, the conditions to mixotrophically metabolize at least one gaseous substrate in the GS and at least one substrate present in the AS are a pH from about 6 to about 8, a temperature from about 30° C. to about 40° C., and a pressure of above 1 atm absolute. In some embodiments, the fermentation zone pressure is above 1 atm absolute, for example above 2 atm absolute, such as above 2.5 atm absolute. In some embodiments, the fermentation zone pressure is from about 1.5 to about 10 atm absolute, such as from about 1.5 to about 8 atm absolute, such as from about 1.5 to about 5 atm absolute, such as from about 2.5 to about 4 atm absolute.

In some embodiments, the conditions to metabolize at least one polyol such glycerol, carbohydrates, or oligomers of carbohydrate, and (2) at least one carboxylic acid such as acetic acid, lactic acid, succinic acid or butyric acid present in the AS are a pH from about 6 to about 8 and a temperature from about 30° C. to about 40° C.

In some embodiments, the fermentation process is aerobic or microaerobic.

In some embodiments, the biocatalytic processes described herein comprise the use of biocatalysts. The term "biocatalyst," as used herein, refers to an isolated or purified enzyme that is in solution or immobilized on a solid substrate, an extracellular enzyme, an enzyme present in a cell lysate, an enzyme produced in situ by a host cell that performs a single chemical transformation of an organic molecule, or a whole cell that catalyzes a series of sequential transformations of one or more organic molecules. In some embodiments, isolated or extracellular enzymes are used as biocatalysts. In some embodiments, whole cells are used as the biocatalyst. In some embodiments, both isolated or extracellular and whole cells are used as biocatalysts. The isolated or purified enzyme may be purchased from commercial sources, or purified from a host cell that expresses the enzyme either naturally, or non-naturally. The host cell may be naturally occurring or recombinant, e.g., an engineered cell. The host cell may be a prokaryote, such as a bacterium or archaeon, or a eukaryote, such as a fungus (e.g., yeast) or an animal cell (e.g., a mammalian cell). The host cell may express and secrete the enzyme, which is capable of catalyzing a particular reaction, e.g., hydrolysis.

In some embodiments, the biocatalytic processes described herein comprise the use of microorganisms, for example naturally occurring microorganisms and recombinant microorganisms, e.g., engineered microorganisms. In some embodiments, the organism comprises at least one of (1) a genetic alteration, (2) a chemical alteration, and (3) a non-naturally occurring alteration.

In some embodiments, the organism or an equivalent or engineered equivalent thereof is a methanotroph, a hydrogen-metabolizing chemolithotrophic organism, or a CO-metabolizing chemolithotrophic organism.

In some embodiments, the organism or an equivalent or engineered equivalent is capable of metabolizing glycerol.

In some embodiments, the organism or an equivalent or engineered equivalent is capable of metabolizing one or more carboxylic acids such as acetic, lactic, or butyric acids.

In some embodiments, the organism is able to metabolize both glycerol and one or more carboxylic acids such as acetic, lactic, or butyric acid.

In some embodiments, the organism is able to metabolize both glycerol and lactic acid.

In some embodiments, the organism is a methanotroph, a hydrogen-metabolizing chemolithotrophic organism, or a CO-metabolizing chemolithotrophic organism that is able to metabolize both glycerol and lactic acid.

The host cell may be a prokaryote, such as a bacterium or archaeon, or a eukaryote, such as a fungus (e.g., yeast) or an animal cell (e.g., a mammalian cell). The host cell may express and secrete the enzyme, which is capable of catalyzing a particular reaction, e.g., hydrolysis. The host cell can contain additional enzymatic pathways that catalyze different reactions. The host cell can contain multiple enzymatic pathways active in the biocatalytic processes described herein.

In some embodiments, the host microorganism is a prokaryote. For example, the prokaryote can be a bacterium from the genus Clostridia, such as *Clostridium ljungdahlii*, *Clostridium autoethanogenum*, or *Clostridium kluyveri*; from the genus *Cupriavidus*, such as *Cupriavidus necator* (also known as *Ralstonia eutropha*) or *Cupriavidus metallidurans*; or a bacterium able to metabolize the same substrates as *Cupriavidus* necator. In some embodiments, the host microorganism is a methanotroph. Such prokaryotes also can be a source of genes to construct recombinant host cells that can be used in biocatalytic processes described herein.

In at least one embodiment, the organism is *Cupriavidus necator* or *clostridium*, or an equivalent, or engineered equivalent thereof. In some embodiments, the host microorganism is a eukaryote.

In some embodiments, the host microorganism is a chemolithotrophic host. In at least one embodiment, the host organism can be a hydrogen-metabolizing chemolithotrophic organism. For example, the host organism can be from the genus *Hydrogenobacter*, such as *Hydrogenobacter thermophiles* or an equivalent or engineered equivalent thereof; or from the genus *Hydrogenophaga*, such as *Hydrogenophaga pseudoflava* or an equivalent or engineered equivalent thereof. For example, the organism can be *Aquaspirillum autotrophicum* or an equivalent or engineered equivalent thereof. In at least one embodiment, the organism can be a CO-metabolizing chemolithotrophic organism.

In some embodiments, the hydrogen-metabolizing chemolithotrophic organism is capable of metabolizing carbon dioxide and hydrogen.

In some embodiments, the hydrogen-metabolizing chemolithotrophic organism is capable of metabolizing carbon dioxide and hydrogen via the Calvin-Benson cycle.

In some embodiments, the fermentation or bio-derived product of the biocatalytic processes described herein comprises a volatile product. By "volatile product," what is meant is a product having a boiling point lower than that of water. In some embodiments, the volatile product is a gas at the conditions of the fermentation zone. In some embodiments, the volatile product comprises an alkene, for example butadiene, isoprene, or isobutene.

In some embodiments, the fermentation or bio-derived product of the biocatalytic processes described herein comprises a single-cell organism or biomass.

In some embodiments, the fermentation or bio-derived product of the biocatalytic processes described herein comprises a single-cell organism or biomass comprising a polyhydroxybutyric acid (PHB).

In some embodiments, the fermentation or bio-derived product of the biocatalytic processes described herein comprises an alkene, for example butadiene, isoprene, or isobutene, or an alkene precursor, for example a 3-hydroxyenoic acid, an enol, or a 3-hydroxyacid.

In some embodiments, the fermentation or bio-derived product of the biocatalytic processes described herein comprises a compound, or a salt thereof, selected from one or more of an amino acid, a hydroxycarboxylic acid, a hydroxylamine, a diamine, a lactam, a carboxylic alcohol, a carboxylic diol, a carboxylic polyol, a carboxylic diamine, or a carboxylic diacid. For example, in some embodiments, the fermentation or bio-derived product comprises a compound, or a salt thereof, selected from one or more of 6-aminohexanoic acid, 7-aminoheptanoic acid, hexamethylenediamine, adipic acid, caprolactam, 1,6-hexanediol, or 1,5-pentamethylene diamine.

The present disclosure includes compositions comprising a fermentation or bio-derived product produced by a biocatalytic process as described herein, as claimed herein, or as shown in any of the Figures. The present disclosure includes compositions comprising an AS, a GS, and an organism, wherein the organism or an equivalent or engineered equivalent thereof is a methanotroph or a hydrogen-metabolizing or CO-metabolizing chemolithotrophic organism, and wherein the organism is capable of mixotrophic metabolism of at least one gaseous substrate in the GS and at least one substrate in the AS.

Also described herein are compositions comprising an AS and a GS, wherein the compositions are suitable to biocatalytic processes as described herein. Also described herein are compositions comprising an AS, a GS, and an organism, wherein the compositions are suitable to biocatalytic processes as described herein. Also described herein are compositions comprising an AS, a GS, an organism, and at least one product of biocatalytic processes as described herein.

The present disclosure includes systems for producing a fermentation or bio-derived product, comprising: a member suitable for providing an AS or derivative thereof to a fermentation zone; a member suitable for providing a GS or derivative thereof to a fermentation zone; a fermentation zone, the fermentation zone comprising at least one organism capable of mixotrophic metabolism of an AS substrate and a GS substrate, wherein the fermentation operates at conditions to simultaneously ferment at least one gaseous substrate in the GS and at least one substrate present in the AS; one of more fermentation zone control members, suitable for controlling the conditions for fermenting; and a zone for treating the product. In some embodiments, the zone for treating the product is optional. In some embodiments the zone for treating the product facilitates a separation step. The AS and GS provided to such systems may be as described previously herein. The at least one organism capable of mixotrophic metabolism may be as described previously herein. The fermentation conditions may be as described previously herein.

The present disclosure includes compositions comprising a fermentation or bio-derived product produced by a biocatalytic process as described herein, as claimed herein, or as shown in any of the Figures. The present disclosure includes compositions comprising an AS comprising (1) at least one polyol such glycerol, carbohydrates, or oligomers of carbohydrate, and (2) a carboxylic acid such as acetic acid, lactic acid, succinic acid or butyric acid or derivative, and an organism, wherein the organism or an equivalent or engineered equivalent thereof is capable of metabolizing (1) at least one polyol such glycerol, carbohydrates, or oligomers of carbohydrate, and (2) a carboxylic acid such as acetic acid, lactic acid, succinic acid or butyric acid or derivative in the AS.

Also described herein are compositions comprising an AS wherein the compositions are suitable to biocatalytic processes as described herein. Also described herein are compositions comprising an AS, and an organism, wherein the compositions are suitable to biocatalytic processes as described herein. Also described herein are compositions comprising an AS, an organism, and at least one product of biocatalytic processes as described herein.

The present disclosure includes systems for producing a fermentation or bio-derived product, comprising: a member suitable for providing an AS or derivative comprising (1) at least one polyol such glycerol, carbohydrates, or oligomers of carbohydrate, and (2) a carboxylic acid such as acetic acid, lactic acid, succinic acid or butyric acid or derivative thereof to a fermentation zone; a fermentation zone, the fermentation zone comprising at least one organism capable of metabolism of at least one polyol such glycerol, carbohydrates, or oligomers of carbohydrate, and (2) a carboxylic acid such as acetic acid, lactic acid, succinic acid or butyric acid, wherein the fermentation operates at conditions to simultaneously ferment at least one polyol such as glycerol, a carbohydrate, or an oligomer of a carbohydrate, and (2) a carboxylic acid such as acetic acid, lactic acid, succinic acid or butyric acid; one of more fermentation zone control members, suitable for controlling the conditions for fermenting; and a zone for treating the product. The AS provided to such systems may be as described previously herein. At least one organism capable of simultaneous metabolism may be as described previously herein. The fermentation conditions may be as described previously herein.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been particularly shown and described with references to preferred embodiments thereof, it will be understood by those skilled in the art that various changes in form and details may be made therein without departing from the scope of the invention encompassed by the appended claims.

EXAMPLES

Comparative Example 1A. Isoprene from Aerobic Fermentation of Glycerol in Thin Stillage The aqueous thin stillage stream containing lactic acid (16.8 g/L) and glycerol (14.4 g/L) from a corn dry mill bioethanol plant producing 50 million gallons of ethanol/year is recovered and fed to an aerobic fermentation utilizing *E. coli* bacteria and maintained at a pH of 6.5 to 7.0 and a temperature of 30° C. Only the glycerol, not the lactic acid, is converted to product. The aerobic fermentation produces 3,500 metric tons/year of isoprene (70% of theoretical yield), and co-produces 5,600 metric tons/year of by-product carbon dioxide that is not utilized (see Table 2).

Example 1B. Isoprene from Aerobic Fermentation of Thin Stillage

The aqueous thin stillage stream of Example 1A is recovered and fed to an aerobic fermentation utilizing *C. necator* bacteria and maintained at a pH of 6.5 to 7.0 and a temperature of 30° C. The aerobic fermentation ferments at least the glycerol and lactic acid from the thin stillage stream to produce 7,200 metric tons/year of isoprene (70% of theoretical yield), a 110% increase (2.1×) in isoprene production relative to Comparative Example 1A, and co-produces 13,500 metric tons/year of by-product carbon dioxide that is not utilized (see Table 2).

Example 1C. Isoprene from Mixotrophic Aerobic Fermentation of Thin Stillage with Hydrogen The aqueous thin stillage stream of Example 1A is recovered and fed to an aerobic fermentation utilizing *C. necator* bacteria and maintained at a pH of 6.5 to 7.0 and a temperature of 30° C. The aerobic fermentation ferments at least the glycerol and lactic acid from the thin stillage stream. Purchased hydrogen is fed to the aerobic fermentation in sufficient quantity to convert approximately 60% of the by-product carbon dioxide from fermentation of the thin stillage. The aerobic fermentation produces 8,900 metric tons/year of isoprene (70% of theoretical yield), a 160% increase (2.6×) in isoprene production relative to Comparative Example 1A, and co-produces 8,700 metric tons/year of by-product carbon dioxide from the thin stillage fermentation that is not utilized (see Table 2).

Example 1D. Isoprene from Mixotrophic Aerobic Fermentation of Thin Stillage and Bioethanol Fermenter Off-Gas Carbon Dioxide with Hydrogen The aqueous thin stillage stream of Example 1A is recovered and fed to a mixotrophic aerobic fermentation utilizing *C. necator* bacteria and maintained at a pH of 6.5 to 7.0 and a temperature of 30° C. The aerobic fermentation ferments at least the glycerol and lactic acid from the thin stillage stream. Approximately a 20% portion of the fermenter off-gas containing carbon dioxide from the corn dry mill bioethanol plant of Example 1A is also recovered and fed to the mixotrophic aerobic fermentation. Purchased hydrogen is also fed to the mixotrophic aerobic fermentation in sufficient quantity to convert approximately 60% of the by-product carbon dioxide from fermentation of the thin stillage and the carbon dioxide in the 20% portion of bioethanol plant fermenter off-gas. The mixotrophic aerobic fermentation produces 12,800 metric tons/year of isoprene (70% of theoretical yield), a 270% increase (3.7×) in isoprene production relative to Comparative Example 1A, and co-produces 8,700 metric tons/year of by-product carbon dioxide from the thin stillage fermentation that is not utilized (see Table 2).

Comparative Example 2A: 7-Aminoheptanoic Acid from Aerobic Fermentation of Glycerol in Thin Stillage The aqueous thin stillage stream containing lactic acid (16.8 g/L) and glycerol (14.4 g/L) from a corn dry mill bioethanol plant producing 50 million gallons of ethanol/year is recovered and fed along with an excess stoichiometric amount of aqueous ammonia to an aerobic fermentation utilizing *E. coli* bacteria and maintained at a pH of 6.5 to 7.0 and a temperature of 30° C. Only the glycerol, not the lactic acid, is converted to product. The aerobic fermentation produces 5,500 metric tons/year of 7-aminoheptanoic acid (70% of theoretical yield), and co-produces 5,000 metric tons/year of by-product carbon dioxide that is not utilized (see Table 2).

Example 2B: 7-Aminoheptanoic Acid from Aerobic Fermentation of Thin Stillage

The aqueous thin stillage stream of Example 2A is recovered and fed along with an excess stoichiometric amount of aqueous ammonia to an aerobic fermentation utilizing *C. necator* bacteria and maintained at a pH of 6.5 to 7.0 and a temperature of 30° C. The aerobic fermentation ferments at least the glycerol and lactic acid from the thin stillage stream to produce 11,600 metric tons/year of 7-aminoheptanoic acid (70% of theoretical yield), a 110% increase (2.1×) in 7-aminoheptanoic acid production relative to Comparative Example 2A, and co-produces 12,000 metric tons/year of by-product carbon dioxide that is not utilized (see Table 2).

Example 2C. 7-Aminoheptanoic Acid from Mixotrophic Aerobic Fermentation of Thin Stillage with Hydrogen The aqueous thin stillage stream of Example 2A is recovered and fed along with an excess stoichiometric amount of aqueous ammonia to an aerobic fermentation utilizing *C. necator* bacteria and maintained at a pH of 6.5 to 7.0 and a temperature of 30° C. The aerobic fermentation ferments at least the glycerol and lactic acid from the thin stillage stream. Purchased hydrogen is fed to the aerobic fermentation in sufficient quantity to convert approximately 60% of the by-product carbon dioxide from fermentation of the thin stillage. The aerobic fermentation produces 14,000 metric tons/year of 7-aminoheptanoic acid (70% of theoretical yield), a 150% increase (2.5×) in 7-aminoheptanoic acid production relative to Comparative Example 2A, and co-produces 7,800 metric tons/year of byproduct carbon dioxide from the thin stillage fermentation that is not utilized (see Table 2).

Example 2D. 7-Aminoheptanoic Acid from Mixotrophic Aerobic Fermentation of Thin Stillage and Bioethanol Fermenter Off-Gas Carbon Dioxide with Hydrogen The aqueous thin stillage stream of Example 2A is recovered and fed along with an excess stoichiometric amount of aqueous ammonia to a mixotrophic aerobic fermentation utilizing C. necator bacteria and maintained at a pH of 6.5 to 7.0 and a temperature of 30° C. The aerobic fermentation ferments at least the glycerol and lactic acid from the thin stillage stream. Approximately a 20% portion of the fermenter off-gas containing carbon dioxide from the corn dry mill bioethanol plant of Example 2A is also recovered and fed to the mixotrophic aerobic fermentation. Purchased hydrogen is also fed to the mixotrophic aerobic fermentation in sufficient quantity to convert approximately 60% of the byproduct carbon dioxide from fermentation of the thin stillage and the carbon dioxide in the 20% portion of bioethanol plant fermenter off-gas. The mixotrophic aerobic fermentation produces 19,900 metric tons/year of 7-aminoheptanoic acid (70% of theoretical yield), a 260% increase (3.6×) in 7-aminoheptanoic acid production relative to Comparative Example 2A, and co-produces 7,800 metric tons/year of by-product carbon dioxide from the thin stillage fermentation that is not utilized (see Table 2).

Comparative Example 3A. Biomass from Aerobic Fermentation of Glycerol in Thin Stillage The aqueous thin stillage stream containing lactic acid (16.8 g/L) and glycerol (14.4 g/L) from a corn dry mill bioethanol plant producing 50 million gallons of ethanol/year is recovered and fed along with an excess stoichiometric amount of aqueous ammonia to an aerobic fermentation utilizing E. coli bacteria and maintained at a pH of 6.5 to 7.0 and a temperature of 30° C. Only the glycerol, not the lactic acid, is converted to product. The aerobic fermentation produces 5,200 metric tons/year of biomass (25% by wt PHB, 70% of theoretical yield), and co-produces 7,000 metric tons/year of by-product carbon dioxide that is not utilized (see Table 2).

Example 3B. Biomass from Aerobic Fermentation of Thin Stillage

The aqueous thin stillage stream of Example 3A is recovered and fed along with an excess stoichiometric amount of aqueous ammonia to an aerobic fermentation utilizing C. necator bacteria and maintained at a pH of 6.5 to 7.0 and a temperature of 30° C. The aerobic fermentation ferments at least the glycerol and lactic acid from the thin stillage stream to produce 11,900 metric tons/year of biomass (25% by wt PHB, 70% of theoretical yield), a 130% increase (2.3×) in biomass (25% by wt PHB) production relative to Comparative Example 3A, and co-produces 14,600 metric tons/year of by-product carbon dioxide that is not utilized (see Table 2).

Example 3C. Biomass from Mixotrophic Aerobic Fermentation of Thin Stillage with Hydrogen The aqueous thin stillage stream of Example 3A is recovered and fed along with an excess stoichiometric amount of aqueous ammonia to an aerobic fermentation utilizing C. necator bacteria and is maintained at a pH of 6.5 to 7.0 and a temperature of 30° C. The aerobic fermentation ferments at least the glycerol and lactic acid from the thin stillage stream. Purchased hydrogen is fed to the aerobic fermentation in sufficient quantity to convert approximately 60% of the by-product carbon dioxide from fermentation of the thin stillage. The aerobic fermentation produces 15,200 metric tons/year of biomass (25% by wt PHB, 70% of theoretical yield), a 190% increase (2.9×) in biomass (25% by wt PHB) production relative to Comparative Example 3A, and co-produces 9,400 metric tons/year of by-product carbon dioxide from the thin stillage fermentation that is not utilized (see Table 2).

Example 3D. Biomass from Mixotrophic Aerobic Fermentation of Thin Stillage and Bioethanol Fermenter Off-Gas Carbon Dioxide with Hydrogen The aqueous thin stillage stream of Example 3A is recovered and fed along with an excess stoichiometric amount of aqueous ammonia to a mixotrophic aerobic fermentation utilizing C. necator bacteria and maintained at a pH of 6.5 to 7.0 and a temperature of 30° C. The aerobic fermentation ferments at least the glycerol and lactic acid from the thin stillage stream. Approximately a 20% portion of the fermenter off-gas containing carbon dioxide from the corn dry mill bioethanol plant of Example 3A is also recovered and fed to the mixotrophic aerobic fermentation. Purchased hydrogen is also fed to the mixotrophic aerobic fermentation in sufficient quantity to convert approximately 60% of the by-product carbon dioxide from fermentation of the thin stillage and the carbon dioxide in the 20% portion of bioethanol plant fermenter off-gas. The mixotrophic aerobic fermentation produces 21,900 metric tons/year of biomass (25% by wt PHB, 70% of theoretical yield), a 320% increase (4.2×) in biomass (25% by wt PHB) production relative to Comparative Example 3A, and co-produces 9,400 metric tons/year of by-product carbon dioxide from the thin stillage fermentation that is not utilized (see Table 2).

TABLE 2

Exemplary aerobic fermentation products and production rates versus comparative production rates for Examples 1A to 3D in a 50 million gal/yr corn dry mill bioethanol plant.

| Example No. | Relevant FIG. No. | Feed streams | Other feed streams | Aerobic fermentation product | Annual Production Rate, (metric tons product/yr) | Annual Production Rate vs. Comparative |
| --- | --- | --- | --- | --- | --- | --- |
| Comparative 1A | 3A | thin stillage (only glycerol converts) | — | isoprene | 3,500 | 1X |
| 1B | 3A | thin stillage (glycerol and lactic acid converts) | — | isoprene | 7,200 | 2.1X (110% increase) |

TABLE 2-continued

Exemplary aerobic fermentation products and production rates versus comparative production rates for Examples 1A to 3D in a 50 million gal/yr corn dry mill bioethanol plant.

| Example No. | Relevant FIG. No. | Feed streams | Other feed streams | Aerobic fermentation product | Annual Production Rate, (metric tons product/yr) | Annual Production Rate vs. Comparative |
|---|---|---|---|---|---|---|
| 1C | 3B | thin stillage (glycerol and lactic acid converts) | H$_2$ | isoprene | 8,900 | 2.6X (160% increase) |
| 1D | 3C | thin stillage (glycerol and lactic acid converts) + 20% of fermenter off-gas | H$_2$ | isoprene | 12,800 | 3.7X (270% increase) |
| Comparative 2A | 3A | thin stillage (only glycerol converts) | NH$_3$(aq) | 7-aminoheptanoic acid | 5,500 | 1X |
| 2B | 3A | thin stillage | NH$_3$(aq) | 7-aminoheptanoic acid | 11,600 | 2.1X (110% increase) |
| 2C | 3B | thin stillage | NH$_3$(aq), H$_2$ | 7-aminoheptanoic acid | 14,000 | 2.5X (150% increase) |
| 2D | 3C | thin stillage + 20% of fermenter off-gas | NH$_3$(aq), H$_2$ | 7-aminoheptanoic acid | 19,900 | 3.6X (260% increase) |
| Comparative 3A | 3A | thin stillage (only glycerol converts) | NH$_3$(aq) | biomass (25 wt % PHB) | 5,200 | 1X |
| 3B | 3A | thin stillage | NH$_3$(aq) | biomass (25 wt % PHB) | 11,900 | 2.3X (130% increase) |
| 3C | 3B | thin stillage | NH$_3$(aq), H$_2$ | biomass (25 wt % PHB) | 15,200 | 2.9X (190% increase) |
| 3D | 3C | thin stillage + 20% of fermenter off-gas | NH$_3$(aq), H$_2$ | biomass (25 wt % PHB) | 21,900 | 4.2X (320% increase) |

What is claimed is:

1. A biocatalytic process comprising:
   providing an aqueous thin stillage stream from a bioethanol production process to a fermentation zone, wherein the aqueous thin stillage stream comprises glycerol and lactic acid;
   providing a gaseous stream to the fermentation zone, wherein the gaseous stream comprises at least one substrate selected from CO$_2$, H$_2$, CO$_2$/H$_2$, methane, and CO, wherein the aqueous thin stillage stream and the gaseous stream are contacted and/or mixed in the fermentation zone; and
   providing a *Cupriavidus necator* to the fermentation zone, wherein the *Cupriavidus necator* mixotrophically metabolizes glycerol and lactic acid in the aqueous thin stillage stream and the at least one substrate in the gaseous stream to produce a product, wherein said product produced is at least 2.1× up to 4.2× more than fermentation in *Escherichia coli*;
   wherein the product comprises 7-aminoheptanoic acid.

2. The biocatalytic process of claim 1, wherein the gaseous stream is natural gas, wherein at least a portion of the gaseous stream is combusted in at least one combined heat and power (CHP) unit to generate power.

3. The biocatalytic process of claim 2, wherein heat from the combined heat and power unit generates steam that drives a turbo generator for generating electric power.

4. The biocatalytic process of claim 1, wherein the gaseous stream is natural gas, wherein at least a portion of the gaseous stream is provided to a gas combustion turbo-generator to generate power.

5. The biocatalytic process of claim 1, wherein the gaseous stream is syngas, wherein at least a portion of the gaseous stream drives a non-combusting turbo-generator to generate power.

6. The biocatalytic process pf claim 1, wherein the gaseous stream is natural gas, wherein at least a portion of the gaseous stream is provided to a steam methane reformation to produce syngas, and at least a portion of the produced syngas is provided to a gas generator to generate power.

7. The biocatalytic process of claim 2, wherein the power generation produces $H_2$ and $O_2$ via water electrolysis, wherein said $H_2$ is provided to the fermentation zone.

8. The biocatalytic process of claim 7, wherein the $O_2$ is provided to the fermentation zone.

9. The biocatalytic process of claim 2, wherein the generated power is: integrated or exported; used in a bio-ethanol production process; provides power for $H_2$ production via water electrolysis, thereby producing $H_2$ for use in the fermentation zone; or a combination thereof.

10. A biocatalytic process comprising:
providing an aqueous thin stillage stream from a bioethanol production process to a fermentation zone, wherein the aqueous thin stillage stream comprises glycerol and lactic acid;
providing a gaseous stream to the fermentation zone, wherein the gaseous stream comprises at least $H_2$, wherein the aqueous thin stillage stream and the gaseous stream are contacted and/or mixed in the fermentation zone;
providing a *Cupriavidus necator* to the fermentation zone, wherein the *Cupriavidus necator* metabolizes glycerol and lactic acid in the aqueous thin stillage stream and the at least one substrate in the gaseous stream to produce a product, wherein said product produced is at least 2.1× up to 4.2× more than fermentation in *Escherichia coli;*
wherein the product comprises 7-aminoheptanoic acid.

11. The biocatalytic process of claim 1, further comprising:
removing a fermentation broth bleed stream from the fermentation zone;
treating the fermentation broth bleed stream to remove biomass and produce a biomass-free broth; and
recycling the biomass-free broth to a fermentation step of the biocatalytic process.

12. The biocatalytic process of claim 1, wherein the gaseous stream substrate in the fermentation zone has a $CO_2$:$H_2$ molar ratio ranging from 0 to 0.35 mol $CO_2$/mol $H_2$.

13. The biocatalytic process of claim 1, wherein the conditions to mixotrophically metabolize at least one gaseous substrate in the gaseous stream and glycerol and lactic acid in the aqueous thin stillage stream are a pH ranging from 6 to 8, a temperature ranging from 30° C. to 40° C., and a pressure of above 1 atm absolute.

14. A biocatalytic process for producing a product, comprising:
providing an aqueous thin stillage stream from a bio-ethanol production process to a fermentation zone, wherein the aqueous thin stillage stream from a bio-ethanol production process comprises (1) at least one glycerol, carbohydrate, or oligomer of carbohydrate, and (2) a carboxylic acid;
providing a gaseous stream comprising at least one of $CO_2$, $H_2$, $CO_2$/$H_2$, methane, and CO to the fermentation zone;
providing a *Cupriavidus necator* to the fermentation zone, wherein the *Cupriavidus necator* mixotrophically metabolizes at least one gaseous substrate in the gaseous stream and (1) at least one glycerol, carbohydrate, or oligomer of carbohydrate, and (2) a carboxylic acid in the aqueous thin stillage stream and forms at least 2.1× up to 4.2× more product via the fermentation as compared to fermentation in *E. coli;*
wherein the product comprises 7-aminoheptanoic acid.

* * * * *